United States Patent [19]

Narayan et al.

[11] 4,284,730

[45] Aug. 18, 1981

[54] LIQUID CARBODIIMIDE- AND URETONIMINE-ISOCYANURATE-CONTAINING POLYISOCYANATE COMPOSITIONS AND MICROCELLULAR FOAMS MADE THEREFROM

[75] Inventors: Thirumurti Narayan, Grosse Ile; Peter T. Kan, Plymouth, both of Mich.

[73] Assignee: BASF Wyandotte Corporation, Wyandotte, Mich.

[21] Appl. No.: 119,273

[22] Filed: Feb. 7, 1980

[51] Int. Cl.$^3$ .................. C08G 18/14; C08G 18/16; C08G 18/79

[52] U.S. Cl. .................... 521/160; 521/161; 521/901; 521/902; 521/107; 252/182; 528/67; 528/73; 521/124; 521/121; 521/128; 521/126; 521/127; 521/125; 521/129; 521/117; 260/453 A; 260/453 P

[58] Field of Search .................. 528/73, 67; 521/160, 521/161; 252/182; 260/453 A, 453 P

[56] References Cited

U.S. PATENT DOCUMENTS

| | | | |
|---|---|---|---|
| 3,723,363 | 3/1973 | Shaw .................................. | 521/160 |
| 3,728,289 | 4/1973 | Reuter et al. ........................ | 521/160 |
| 3,970,618 | 7/1976 | Jabs et al. ........................... | 521/161 |
| 4,014,935 | 3/1977 | Ibbotson ............................. | 528/67 |
| 4,067,820 | 1/1978 | Wagner et al. ..................... | 252/426 |

FOREIGN PATENT DOCUMENTS 1356851  6/1974  United Kingdom ........................ 521/161

*Primary Examiner*—H. S. Cockeram
*Attorney, Agent, or Firm*—Norbert M. Lisicki

[57] ABSTRACT

The invention relates to carbodiimide- and/or uretonimine-isocyanurate-containing polyisocyanates, to the process for their preparation, and to microcellular foams prepared therefrom.

These compositions may be prepared in the presence of the appropriate catalyst by (a) a partial trimerization of a mixture of polyisocyanate and carbodiimide and uretonimine containing polyisocyanate with trimer catalyst to the desired free isocyanate level, (b) sequential, partial carbodiimidization followed by partial trimerization of a polyisocyanate to the desired free isocyanate level (c) sequential partial trimerization of a polyisocyanate followed by partial carbodiimidization, (d) simultaneous conversion using the mixed catalyst system of carbodiimide and isocyanurate catalysts reacted to the desired free isocyanate level, and (e) blending liquid polyisocyanate with the carbodiimide and uretonimine containing polyisocyanate and isocyanurate containing polyisocyanate to the desired isocyanate level.

50 Claims, No Drawings

LIQUID CARBODIIMIDE- AND URETONIMINE-ISOCYANURATE-CONTAINING POLYISOCYANATE COMPOSITIONS AND MICROCELLULAR FOAMS MADE THEREFROM

BACKGROUND OF THE INVENTION

1. Field of the Invention

The present invention relates to carbodiimide- and uretonimine-isocyanurate-containing polyisocyanates, to the process for the preparation thereof and to microcellular foams and elastomers prepared from said modified polyisocyanate compositions. More particularly, the invention relates to polyisocyanate compositions containing carbodiimide and uretonimine and isocyanurate linkages prepared by reacting organic polyisocyanates in the presence of catalysts which convert isocyanate groups to carbodiimide groups and in the presence of catalysts which promote the trimerization of isocyanate groups to isocyanurate.

2. Description of the Prior Art

Carbodiimide- and uretonimine-containing isocyanates are known in the prior art and have been prepared employing a variety of processes. Further, isocyanurate-modified polyisocyanate compositions and processes for the preparation thereof have been reported. Rigid low density foams containing carbodiimide and isocyanurate linkages are known. Among the references which can be cited are the following: U.S. Pat. No. 4,085,140 which discloses a process for the conversion of isocyanate groups to carbodiimide groups employing a co-catalyst system. U.S. Pat. No. 4,031,026 teaches a diphenylmethane diisocyanate composition which comprises diphenylmethane diisocyanate, a diphenylmethane diisocyanate uretonimine group containing derivative, a reaction product of MDI of the diphenylmethane diisocyanate and a diol, and methylene bridged polyphenol polyisocyanate. U.S. Pat. No. 3,996,223 teaches a process for the production of organic polyisocyanates containing isocyanurate structure by polymerizing said organic polyisocyanate in the presence of catalysts which cause the formation of trimers. U.S. Pat. No. 3,657,161 claims a polycarbodiimide polyisocyanurate foam and a process for preparing the same which comprises polymerizing an organic polyisocyanate in the presence of a blowing agent, a catalyst which promotes the formation of carbodiimide groups and a catalyst which promotes the simultaneous formation of isocyanurate groups. U.S. Pat. No. 4,085,140 teaches the preparation of carbodiimide-containing polyisocyanates suitable for the preparation of microcellular foams or elastomers. Applicants are unaware of any art which teaches or even suggests the compositions and process for the preparation thereof of stable liquid polyisocyanate compositions which contain both carbodiimide or uretonimine and isocyanurate linkages and the foams prepared therefrom.

SUMMARY OF THE INVENTION

The present invention relates to the compositions of stable liquid polyisocyanate compositions in which some of the polyisocyanate has been converted to carbodiimide- and uretonimine- and isocyanurate-containing polyisocyanate, to the processes for the preparation thereof, and to microcellular foams and elastomers prepared therefrom.

DESCRIPTION OF THE PREFERRED EMBODIMENTS

The present invention deals with modified stable liquid polyisocyanate compositions comprising carbodiimide- and uretonimine-isocyanurate-containing polyisocyanates. These polyisocyanate compositions are generally clear, low-viscosity liquids displaying excellent room temperature storage stability. The carbodiimide and uretonimine structure exists in equilibrium as shown below.

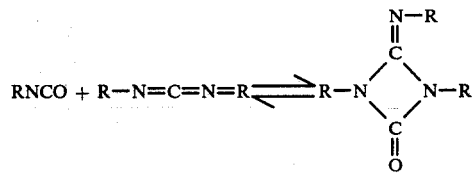

The isocyanurate compounds, also called trimers, have the following structure

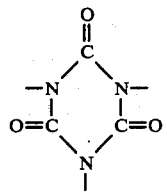

These compositions are suitable for the preparation of polyurethane forms and microcellular elastomers which display inproved properties over those obtained in employing modified isocyanates of the prior art. The composition of the instant invention may be prepared in the presence of the appropriate catalysts by (a) partial trimerization of a mixture of polyisocyanate and polyisocyanate-uretonimine with trimer catalysts to the desired free isocyanate level, (b) sequential partial carbodiimidization to uretonimine followed by partial trimerization of a polyisocyanate, (c) sequential trimerization of the polyisocyanate followed by partial carbodiimidization, (d) simultaneous conversion using the mixed catalyst system of carbodiimide and isocyanurate catalysts, (e) blending liquid polyisocyanate with a polyisocyanate-uretonimine mixture and a polyisocyanate-isocyanurate mixture.

The organic polyisocyanate employed in the instant invention corresponds to the formula R'(NCO)z where R' is a polyvalent organic radical which is either aliphatic, arylalkyl, alkylaryl, aromatic or mixtures thereof and z is an integer which corresponds to the valence of R' and is at least 2. Representative of the organic polyisocyanates contemplated herein includes, for example, the aromatic isocyanates such as 2,4-toluenediisocyanate, 2,6-toluene diisocyanate, mixtures of 2,4- and 2,6-toluene diisocyanate, crude toluene diisocyanate, 4,4'-diphenylmethane diisocyanate, 2,4-diphenylmethane diisocyanate, mixtures of 4,4'- and 2,4'-diphenylmethane diisocyanate and the like; the aromatic triisocyanates include such as 4,4',4''-triphenylmethane triisocyanate, 2,4,6-toluene triisocyanate; the aromatic tetraisocyanates such as 4,4'-dimethyl-2,2',5,5'-diphenylmethane tetraisocyanate and the like; arylalkyl polyisocyanates such as xylylene diisocyanate; aliphatic polyisocyanates such as 1,6-hexamethylene diisocyanates, and the like; and mixtures thereof. Other polyisocyanates include polymethylene polyphenylene polyisocyanates, hydrogenated methylene diphenylene diisocyanate, hydrogenated toluene diisocyanate, m-phenylene diisocyanate, 1,5-naphthylene diisocyanate, 2,4-methoxyphenylene diisocyanate, 4,4'-biphenyl diisocyanate, 3,3'-dimethyl-4,4'-biphenyl diisocyanate, and 3,3'-dimethyl-4,4'-diphenylmethane diisocyanate. These polyisocyanates are prepared by conventional methods known to the art such as phosgenation of the corresponding organic amines. The most preferred polyisocyanates are 4,4'-diphenylmethane diisocyanate, polymethylene polyphenylene polyisocyanate, 2,4-toluene diisocyanate, 2,6-toluene diisocyanate and mixtures thereof, or crude toluene diisocyanate.

The polyisocyanate compositions of the instant invention may be prepared by employing well-known carbodiimide-promoting compounds as catalysts and other well-known compounds as trimerization catalysts. The carbodiimide catalysts employed in accordance with the invention can be any of those known in the art as being useful in the conversion of an isocyanate to the corresponding carbodiimide. Illustrative of such catalysts are:

(a) phospholene 1-oxides and 1-sulfides having the formulae:

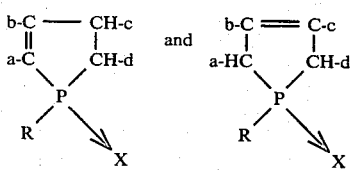

wherein a, b, c, and d are each selected from the group consisting of hydrogen and hydrocarbyl from 1 to 12 carbon atoms inclusive, R is selected from the group consisting of lower alkyl and aryl and X is selected from the group consisting of oxygen and sulfur. The above phospholene compounds and methods for their preparation are described in U.S. Pat. Nos. 2,663,737; 2,663,738; and 2,853,473. The 3-phospholenes can be isomerized readily to the corresponding 2-phospholenes by thermal-treatment or by refluxing with an aqueous base as disclosed by Quinn et al, Journal American Chemical Society, 33, 1024, 1968. Representative compounds within the above class are 1-phenyl-2-phospholene-1-oxide; 3-methyl-1-phenyl-2-phospholene-1-oxide; 1-phenyl-2-phospholene-1-sulfide; 1-ethyl-2-phospholene-1-oxide; 1-ethyl-3-methyl-2-phospholene-1-oxide; 1-ethyl-3-methyl-2-phospholene-1-sulfide; and the isomeric phospholanes corresponding to the above-named compounds. Also, polymer bound phospholene oxide may be employed specifically those having recurring units, for example,

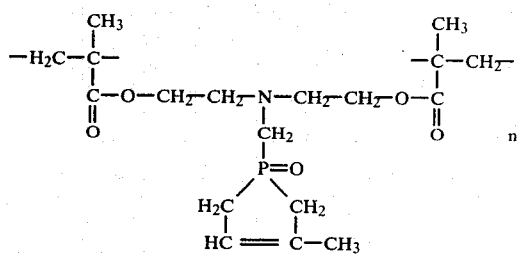

as disclosed in U.S. Pat. No. 4,105,643, and those of the following structure as disclosed in U.S. Pat. No. 4,105,642.

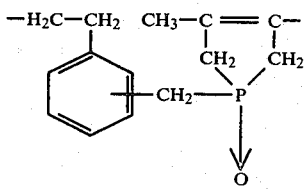

(b) diaza- and oxaza-phospholanes and -phosphorinanes

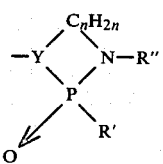

wherein $C_nH_{2n}$ represents alkylene from 1 to 12 carbon atoms, inclusive, at least one and not more than three adjacent carbon atoms and said alkylene radical forming a chain, one end of which is attached to Y, the other end of which is attached to N, thereby completing the heterocyclic ring; R' is selected from the group consisting of hydrocarbyl containing 1 to 12 carbon atoms, inclusive; and halo, nitro, alkoxy, alkyl, mercapto, and cyano-substituted hydrocarbyl from 1 to 12 carbon atoms, inclusive; R" is hydrocarbyl containing from 1 to 12 carbon atoms, inclusive, and Y is selected from the group consisting of —O— and —NR"— wherein R" has the significance as defined above. The above compounds and methods for their preparation are described in U.S. Pat. No. 3,522,303. Representative examples of such compounds are: 2-ethyl-1,3-dimethyl-1,3,2-diazaphospholane-2-oxide; 2-chloromethyl-1,3-dimethyl-1,3,2-diazaphospholane-2-oxide; 2-trichloromethyl-1,3-dimethyl-1,3,2-diazaphospholane-2-oxide; 2-phenyl-1,3-dimethyl-1,3,2-diazaphospholane-2-oxide; 2-phenyl-1,3-dimethyl-1,3,2-diaza-phosphorinane-2-oxide; 2-benzyl-1,3-dimethyl-1,3,2-diazaphospholane-2-oxide; 2-allyl-1,3-dimethyl-1,3,2-diazaphospholane-2-oxide; 2-bromomethyl-1,3-dimethyl-1,3,2-diazaphospholane-2-oxide; 2-cyclohexyl-1,3-dimethyl-1,3,2-diazaphospholane-2-oxide; 2-(2-ethoxyethyl)-1,3-dimethyl-1,3,2-diazaphospholane-2-oxide; and 2-naphthyl-1,3-dimethyl-1,3,2-diazaphospholane-2-oxide.

(c) Triaryl arsines wherein the aryl groups are free from substituents containing reactive hydrogen atoms, said arsine being represented by the formula:

wherein each of R, $R_1$ and $R_2$ represents the same or different aryl moieties having from 6 to 12 carbon atoms, inclusive. Such compounds are described in U.S. Pat. No. 3,406,198. Representative examples are: triphenylarsine, tris(p-tolyl)arsine, tris(p-methoxyphenyl)arsine, tris(p-ethoxyphenyl)arsine, tris(p-chlorophenyl)arsine, tris(p-fluorophenyl)arsine, tris(2,5-xylyl)arsine, tris(p-cyanophenyl)arsine, tris(1-naphthyl)arsine, tris(p-methylmercaptophenyl)arsine, tris(p-biphenylyl)arsine, p-chlorophenylbis(p-tolyl)arsine and phenyl(p-chlorophenyl) (p-bromophenyl)arsine.

(d) Also included are compounds of the formula:

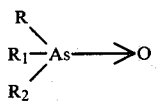

wherein each R, $R_1$ and $R_2$ represents the same or different alkyl or aryl groups having from 6 to 12 carbon atoms, inclusive. Representative examples of such are: triphenylarsine oxide, triethylarsine oxide, and polymer bound arsine oxide such as are described in U.S. Pat. No. 4,143,063:

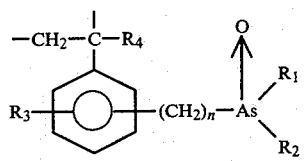

wherein $R_1$ and $R_2$ are hydrocarbyl from 1 to 12 carbon atoms inclusive, $R_3$ is hydrogen, chloro or methyl, $R_4$ is hydrogen or methyl, and n is 0 or 1.

(e) Metallic derivatives of acetylacetone such as the beryllium, aluminum, zirconium, chromium, and iron derivatives thereof as disclosed in U.S. Pat. No. 3,152,131.

(f) Phosphate esters of the formula:

(RO)$_3$PO wherein R is hydrocarbyl from 1 to 12 carbon atoms, inclusive. Such esters and methods for their preparation are disclosed in U.S. Pat. No. 3,056,835. Representative examples are trimethylphosphate, triethylphosphate, ethyldipropylphosphate, triisopropylphosphate, triallylphosphate, triphenylphosphate, and tricresylphosphate.

(g) Phosphine oxides of the formula:

$R_3PO$ wherein R is hydrocarbyl from 1 to 12 carbon atoms, inclusive. Representative examples are triethylphosphine oxide, tributylphosphine oxide, triphenylphosphine oxide, and tris(chloromethyl)phosphine oxide.

(h) Metal complexes derived from a d-group transition element and π-bonding ligand selected from the group consisting of carbon monoxide, nitric oxide, hydrocarbylisocyanides, trihydrocarbylphosphine, trihydrocarbylarsine, trihydrocarbylstilbine, and dihydrocarbylsulfide wherein hydrocarbyl in each instance contains from 1 to 12 carbon atoms, inclusive, provided that at least one of the π-bonding ligands in the complex is carbon monoxide or hydrocarbylisocyanide. Such complexes and methods for the preparation are disclosed in U.S. Pat. No. 3,406,197. Representative examples of such complexes are iron pentacarbonyl, di-iron pentacarbonyl, tungsten hexacarbonyl, molybdenum hexacarbonyl, chromium hexacarbonyl, dimanganese decacarbonyl, nickel tetracarbonyl, ruthenium pentacarbonyl, and the complex of iron tetracarbonyl:methylisocyanide.

The term "hydrocarbyl" from 1 to 12 carbon atoms inclusive employed herein means the monovalent radical obtained by removing one hydrogen atom from a parent hydrocarbon having the stated carbon atom content. Illustrative of such groups are alkyl such as methyl-, ethyl-, propyl-, butyl-, pentyl-, hexyl-, heptyl-, octyl-, nonyl-, decyl-, undecyl-, undodecyl-, including isomeric forms thereof; alkenyl such as allyl, butenyl, pentenyl, hexenyl, heptenyl, octenyl, nonenyl, decenyl, undecenyl, and dodecenyl, including isomeric forms thereof; cycloalkyl such as cyclobutyl, cyclopentyl, cyclohexyl, cycloheptyl, cyclooctyl, and the like; cycloalkenyls such as cyclopentenyl, cyclohexenyl, cycloheptenyl, and the like; aralkyl such as benzyl, phenethyl, phenylpropyl, benzhydryl, naphthylmethyl, and the like; and aryls such as phenyl, tolyl, xylyl, naphthyl, biphenylyl, and the like.

The term "lower alkyl", as used herein, means alkyl from 1 to 6 carbon atoms, inclusive, such a methyl, ethyl, propyl, butyl, pentyl, hexyl and isomeric forms thereof.

The preferred carbodiimide catalysts for use in preparing the compounds of the instant invention are the 2-phospholenes. The most preferred carbodiimide catalysts for use in preparing these compounds in accordance with the invention are the 1-aryl-3-lower alkyl-2-phospholene 1-oxide and 1,3-di(lower alkyl)-2-phospholene 1-oxide. The most preferred species are 1-phenyl-3-methyl-2-phospholene 1-oxide and 1-ethyl-3-methyl-2-phospholene-1-oxide, and the tris(chloromethyl)phosphine oxide. Organotin compounds may also be employed in the present invention.

(i) Organotin compounds.

The organotin compounds which may be employed in the present invention are both quadrivalent and divalent organotin compounds as disclosed in pending application, Ser. No. 67,793, filed Aug. 20, 1975. The quadrivalent organotin compound may be described by the following formula:

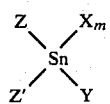

wherein Z and Z' are individually alkyl, aryl, alicyclic, heterocyclic, oxyalkyl or acyloxy group having from 1 to 18 carbon atoms and may be the same or different, X is an alkyl, aryl, alicyclic, heterocyclic, oxyalkyl, acyloxy, thioalkyl or thioalkylene acyloxy group having 1 to 18 carbon atoms, Y is equal to X or oxy groups or a group represented by the following formula:

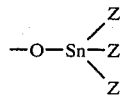

provided that when Y is this group, X is an alkyl or aryl group, m is equal to 1 except when Y is an oxy group then m is equal to 0, and a divalent organotin compound which may be described by the following formula:

wherein Z" is alkyl, aryl, alicyclic, heterocyclic having from 1 to 18 carbon atoms.

Those quadrivalent organotin compounds which may be employed as described in the formula above, are dibutyltin dilaurate, dibutyltin diacetate, dibutyltin di(2-ethylhexanoate), dioctyltin dilaurate, dibutyltin maleate, di(n-octyl)tin maleate, bis(dibutylacetoxytin) oxide, bis(dibutyllauroyloxytin) oxide, dibutyltin dibutoxide, dibutyltin dimethoxide, dibutyltin disalicilate, dibutyltin bis(isooctylmaleate), dibutyltin bis(isopropylmaleate), dibutyltin oxide, tributyltin acetate, tributyltin isopropyl succinate, tributyltin linoleate, tributyltin nicotinate, dimethyltin dilaurate, dimethyltin oxide, dioctyltin oxide, bis(tributyltin) oxide, diphenyltin oxide, triphenyltin acetate, tri-n-propyltin acetate, tri-n-propyltin laurate, and bis(tri-n-propyltin) oxide, dibutyltin dilauryl mercaptide, dibutyltin bis(isooctylmercaptoacetate) and bis(triphenyltin)oxide. Those preferred are dibutyltin diacetate, dibutyltin dilaurate, dibutyltin dilaurylmercaptide, dibutyltin bis(isooctylmercaptoacetate), dibutyltin oxide, bis(triphenyltin) oxide, bis(tri-n-butyltin) oxide. Those divalent organotin compounds which may be employed as catalysts as described in the formula above are: stannous oxalate, stannous oleate, stannous naphthenate, stannous acetate, stannous butyrate, stannous 2-ethylhexanoate, stannous laurate, stannous palmitate, and stannous stearate. The preferred divalent tin compounds are stannous oxalate, stannous oleate and stannous 2-ethylhexanoate.

The trimerization catalysts which may be employed are those well known in the art. Examples of these catalysts are (a) organic strong bases, (b) tertiary amine co-catalyst combinations, (c) Friedel Craft catalysts, (d) basic salt of carboxylic acids, (e) alkali metal oxides, alkali metal alcoholates, alkali metal phenolates, alkali metal hydroxides and alkali metal carbonates, (f) onium compounds from nitrogen, phosphorus, arsenic, antimony, sulfur and selenium, and (g) mono-substituted monocarbamic esters. These include 1,3,5-tris(N,N-dialkylaminoalkyl)-s-hexahydrotriazines; the alkylene oxide and water additives of 1,3,5-tris(N,N-dialkylaminoalkyl)-s-hexahydrotriazines; 2,4,6-tris(dimethylaminomethyl)phenol; ortho, para- or a mixture of o- and p-dimethylaminomethyl phenol and triethylenediamine or the alkylene oxide and water additives thereof, alkali metal carboxylates such as lead octanoate, alkali metal alkoxides, salts of hydroxamic acid, and organic boron-containing compounds. The concentration of trimerization catalysts may be employed in the present invention is from 0.1 part to 20 parts of catalyst per 100 parts of organic polyisocyanate. The temperature ranges which may be employed for the trimerization reaction may range from 25° C. to 230° C., preferably from 60° C. to 120° C. The temperature ranges which may be employed for the carbodimide formation reaction ranges from 50° C. to 250° C., preferably from 60° C. to 230° C.

It is contemplated that the composition of the organic polyisocyanates which are claimed in the instant invention have an unconverted polyisocyanate content ranging from 50 to 99 weight percent of that due to the original total weight of organic polyisocyanate present. The modified portion of the organic polyisocyanate thus ranges from 50 percent to 1 percent. Of the modified portion of the organic polyisocyanate composition, the amount of polyisocyanurate-containing polyisocyanate may range from 1 to 99 weight percent of the modified portion. Concurrently, the carbodiimide- and uretonimine-containing polyisocyanate would then range from 99 to 1 weight percent of the modified portion of the organic polyisocyanates.

In accordance with the present invention, rigid and flexible and microcellular foams may be prepared by the catalytic reaction of the modified organic polyisocyanate with polyols in the presence of blowing agents, surfactants and other additives which may be deemed necessary. Typical polyols which may be employed in the preparation of the foams of the instant invention include polyhydroxyl-containing polyesters, polyoxyalkylene polyether polyols, polyhydroxy-terminated polyurethane polymers, polyhydroxyl-containing phosphorus compounds, and alkylene oxide adducts of polyhydric sulfur-containing esters, polyacetals, aliphatic polyols or diols, ammonia, and amines including aromatic, aliphatic and heterocyclic amines as well as mixtures thereof. Alkylene oxide adducts of compounds which contain two or more different groups within the above-defined classes may also be used such as amino alcohols which contain an amino group and a hydroxyl group. Also, alkylene oxide adducts of compounds which contain one —SH group and one —OH group as well as those which contain an amino group and a —SH group may be used. Generally, the equivalent weight of the polyols will vary from 100 to 10,000, preferably from 1000 to 3000.

Any suitable hydroxy-terminated polyester may be used such as are obtained, for example, from polycarboxylic acids and polyhydric alcohols. Any suitable polycarboxylic acid may be used such as oxalic acid, malonic acid, succinic acid, glutaric acid, adipic acid, pimelic acid, suberic acid, azelaic acid, sebacic acid, brassylic acid, thapsic acid, maleic acid, fumaric acid, glutaconic acid, alpha-hydromuconic acid, beta-hydromuconic acid, alpha-butyl-alpha-ethyl-glutaric acid, alpha,beta-diethylsuccinic acid, isophthalic acid, terephthalic acid, hemimellitic acid, and 1,4-cyclohexanedicarboxylic acid. Any suitable polyhydric alcohol may be used such as ethylene glycol, propylene glycol, trimethylene glycol, 1,2-butanediol, 1,3-butanediol, 1,4-butanediol, 1,2-pentanediol, 1,4-pentanediol, 1,5-pentanediol, 1,6-hexanediol, 1,7-heptanediol, glycerol, 1,1,1-trimethylolpropane, 1,1,1-trimethylolethane, 1,2,6-hexanetriol, alpha-methyl glucoside, pentaerythritol, and sorbitol. Also included within the term "polyhydric alcohol" are compounds derived from phenol such as 2,2-bis(4-hydroxyphenyl)propane, commonly known as Bisphenol A.

Any suitable polyoxyalkylene polyether polyol may be used such as the polymerization product of an alkylene oxide with a polyhydric alcohol. Any suitable polyhydric alcohol may be used such as those disclosed above for use in the preparation of the hydroxy-terminated polyesters. Any suitable alkylene oxide may be used such as ethylene oxide, propylene oxide, butylene oxide, amylene oxide, and mixtures of these oxides. The polyalkylene polyether polyols may be prepared from other starting materials such as tetrahydrofuran and alkylene oxide-tetrahydrofuran mixtures; epihalohydrins such as epichlorohydrin; as well as aralkylene oxides such as styrene oxide. The polyalkylene polyether polyols may have either primary or secondary hydroxyl groups. Included among the polyether polyols are polyoxyethylene glycol, polyoxypropylene glycol, polyoxybutylene glycol, polytetramethylene glycol, block copolymers, for example, combinations of polyoxypropylene and polyoxyethylene glycols, poly-1,2-oxybutylene and polyoxyethylene glycols, poly-1,4-tetramethylene and polyoxyethylene glycols, and copolymer glycols prepared from blends or sequential addition of two or more alkylene oxides. The polyalkylene polyether polyols may be prepared by any known process such as, for example, the process disclosed by Wurtz in 1859 and *Encyclopedia of Chemical Technology*, Vol. 7, pp. 257–262, published by Interscience Publishers, Inc. (1951) or in U.S. Pat. No. 1,922,459. Polyethers which are preferred include the alkylene oxide addition products of trimethylolpropane, glycerine, pentaerythritol, sucrose, sorbitol, propylene glycol, and 2,2-bis(4-hydroxyphenyl)propane and blends thereof having equivalent weights of from 100 to 5000.

Suitable polyhydric polythioethers which may be condensed with alkylene oxides include the condensation product of thiodiglycol or the reaction product of a dicarboxylic acid such as is disclosed above for the preparation of the hydroxyl-containing polyesters with any other suitable thioether glycol.

The hydroxyl-containing polyester may also be a polyester amide such as is obtained by including some amine or amino alcohol in the reactants for the preparation of the polyesters. Thus, polyester amides may be obtained by condensing an amino alcohol such as ethanolamine with the polycarboxylic acids set forth above or they may be made using the same components that make up the hydroxyl-containing polyester with only a portion of the components being a diamine such as ethylene diamine.

Polyhydroxyl-containing phosphorus compounds which may be used include those compounds disclosed in U.S. Pat. No. 3,639,542. Preferred polyhydroxyl-containing phosphorus compounds are prepared from alkylene oxides and acids of phosphorus having a $P_2O_5$ equivalency of from about 72 percent to about 95 percent.

Suitable polyacetals which may be condensed with alkylene oxides include the reaction product of formaldehyde or other suitable aldehyde with a dihydric alcohol or an alkylene oxide such as those disclosed above.

Suitable aliphatic thiols which may be condensed with alkylene oxides include alkanethiols containing at least two —SH groups as 1,2-ethanedithiol, 1,2-propanedithiol, 1,3-propanedithiol, and 1,6-hexanedithiol; alkene thiols such as 2-butene-1,4-dithiol; and alkyne thiols such as 3-hexyne-1,6-dithiol.

Suitable amines which may be condensed with alkylene oxides include aromatic amines such as aniline, o-chloroaniline, p-aminoaniline, 1,5-diaminonaphthalene, methylene dianiline, the condensation products of aniline and formaldehyde, and diaminotoluene; aliphatic amines such as methylamine, triisopropanolamine, ethylenediamine, 1,3-diaminopropane, 1,3-diaminobutane, and 1,4-diaminobutane.

The polyurethane foams of the present invention may also be prepared by the reaction of a graft copolymer polyol with the carbodiimide- and uretonimine-isocyanurate-containing polyisocyanate of the instant invention in the presence of a blowing agent and optionally in the presence of additional polyhydroxyl-containing components, chain-extending agents, catalysts, surface-active agents, stabilizers, dyes, fillers and pigments. Suitable processes for the preparation of cellular polyurethane plastics are disclosed in U.S. Pat. No. Re. 24,514 together with suitable machinery to be used in conjunction therewith. For the preparation of microcellular foams, blowing agents are generally not necessary. If desired for more expanded foams, they may be employed. When water is added as the blowing agent, corresponding quantitites of excess isocyanate to react with the water and product carbon dioxide may be used.

It is possible to proceed with the preparation of the polyurethane plastics by a prepolymer technique wherein an excess of organic polyisocyanate of the instant invention is reacted in a first step with a polyol to prepare a prepolymer having free isocyanate groups which is then reacted in a second step with water to prepare a foam. Alternately, the components may be reacted in a single working step commonly known as the "one-shot" technique of preparing polyurethanes. Furthermore, instead of water, low boiling hydrocarbons such as pentane, hexane, heptane, pentene, and heptene; azo compounds such as azohexahydrobenzodinitrile; halogenated hydrocarbons such as dichlorodifluoromethane, trichlorofluoromethane, dichlorodifluoroethane, vinylidene chloride, and methylene chloride may be used as blowing agents.

Chain-extending agents which may be employed in the preparation of the polyurethane foams include those compounds having at least two functional groups bearing active hydrogen atoms such as water, hydrazine, primary and secondary diamines, amino alcohols, amino acids, hydroxy acids, glycols, or mixtures thereof. A preferred group of chain-extending agents includes water, ethylene glycol, 1,4-butanediol, and primary and secondary diamines which react more readily with the polyisocyanates of the instant invention than does water. These include phenylenediamine, ethylenediamine, diethylenetriamine, N-(2-hydroxypropyl)-ethylenediamine, N,N'-di(2-hydroxypropyl)ethylenediamine, piperazine, and 2-methylpiperazine.

Any suitable catalyst may be used including tertiary amines such as, for example, triethylenediamine, N-methylmorpholine, N-ethylmorpholine, diethylaminoethanol, N-laurylmorpholine, 1-methyl-4(dimethylaminoethyl)piperazine, 3-methoxy-N,N'-dimethylpropylamine, N,N,N'-trimethylisopropylpropylenediamine, N,N,N',N'-tetraethylpropylenediamine, dimethylbenzylamine, and the like. Other suitable catalysts are, for example, tin compounds such as stannous chloride, tin salts of carboxylic acids, such as dibutyltin di-2-ethyl hexanoate and stannous octoate, as well as other organo metallic compounds such as are disclosed in U.S. Pat. No. 2,846,408.

If desired, a surface-active agent may be employed. Numerous surface-active agents have been found satisfactory. Nonionic surfactants are preferred. Of these, the nonionic surface-active agents prepared by the sequential addition of propylene oxide and then ethylene oxide to propylene glycol and the solid or liquid organosilicones have been found particularly desirable. Other surface-active agents which are operative, although not preferred, include polyethylene glycol ethers of long chain alcohols, tertiary amine or alkylolamine salts of long chain alkyl acid sulfate esters, alkylsulfonic esters, and alkylarylsulfonic acids.

The following examples illustrate the nature of the invention. All parts are by weight unless otherwise stated.

The following abbreviations are employed in the Examples below.

Isonate ®125M—pure 4,4'-diphenylmethane diisocyanate (MDI).
Isonate ®143L—carbodiimide- and uretonimine-containing MDI.
Polyol A—a polyoxypropylene-polyoxyethylene glycol, equivalent weight 2200 containing 20 percent by weight ethylene oxide.
Polyol B—a trimethylolpropane, propylene oxide, ethylene oxide adduct, equivalent weight 2243 containing 15 percent ethylene oxide.
I-460—25 percent by weight solution of triethylenediamine in 1,4-butanediol.
T12—dibutyltin dilaurate.

EXAMPLES 1-4

Into a three-liter reaction vessel equipped with a thermometer, inlet for nitrogen, mechanical stirrer, and an air condenser to which is attached a Drierite-packed tube, was added a mixture of 1200 grams of ISONATE 125M and 400 grams of ISONATE 143L, and 0.13 gram of lead octanoate catalyst. The contents were heated to 100° C. and maintained thereat for 195 minutes. The conversion of the reaction mixture to the isocyanurate-containing derivative was followed by determining the drop in the isocyanate value of aliquot samples at 30 minute intervals. The isocyanate value of the reaction mixture as the start was 31.8; after 30 minutes, 31.6; 60 minutes, 31.3; 90 minutes, 31.0; 120 minutes, 30.8; 150 minutes, 30.7; 180 minutes, 30.3; 195 minutes, 30.2. After 195 minutes, 0.4 gram of benzoyl chloride was added to deactivate the catalyst and the mixture was allowed to cool to room temperature. The Brookfield viscosity of the product was about 70 centipoises at 25° C. Examination by infra-red indicates the presence of isocyanate groups carbodiimide and, uretonimine groups and isocyanurate groups. The isocyanate content and viscosity of the product was determined after storage for 60 days at ambient temperature conditions and no change in either the isocyanate content or the viscosity was found. A number of compositions differing in the final isocyanate content was made employing the apparatus of Example 1. These details are summarized in Table I below.

TABLE I

| Example | Polyisocyanate/Parts | Time/Temp. (min./°C.) | % NCO | Viscosity cps. | Catalyst ppm |
|---|---|---|---|---|---|
| 1 | Isonate 125 M/1200 Isonate 143 L/400 | 195/100 | 30.2 | 70 | 12.5 |
| 2 | Isonate 125 M/1200 Isonate 143 L/400 | 52/220 | 27.3 | — | 75.0 |
| 3 | Isonate 125 M/1200 Isonate 143 L/400 | 60/220 | 28.5 | — | 56.0 |
| 4 | Isonate 125 M/300 Isonate 143 L/100 | 90/100 | 29.2 | — | 25.0 |

EXAMPLE 5

Into a reaction vessel equipped similar to that of Example 1, was placed a mixture of 800 grams of molten diphenylmethane diisocyanate and 800 grams of ISONATE 143L. After adding 0.2 grams of lead octonate, the mixture was heated to 100° C. and maintained thereat for 180 minutes. Isocyanate value was determined in a manner similar to that of Example 1. After 180 minutes, an isocyanate value of 29.0 was obtained and 0.6 grams of benzoyl chloride was added to deactivate the catalyst and the mixture was allowed to cool to room temperature. Infra-red analysis of the product indicated the presence of carbodiimide and uretonimine and isocyanurate groups.

EXAMPLE 6

Into a 1000 milliliter flask equipped with a stirrer, thermometer, nitrogen inlet, equipped with a hydrogen inlet, condenser equipped with a Drierite-packed tube was placed 500 grams of molten MDI. The contents were heated to 230° C. and 0.03 grams of tris(chloromethyl)phosphine oxide was added, and the mixture was maintained at that temperature for one hour at which time the isocyanate value dropped at 31.7 percent. The reaction contents were cooled rapidly to about 50° C. and 0.3 gram of lead octanoate was added. The mixture was then heated to 100° C. for one hour at which time the isocyanate content of the mixture dropped to 29.0 percent by weight. Benzoyl chloride, 0.4 grams, was added to deactivate the catalyst and the mixture was allowed to cool to room temperature. Infra-red examination of the mixture indicated the presence of carbodiimide and uretonimine and isocyanurate groups.

EXAMPLE 7

Into a reaction vessel equipped as disclosed in Example 1, 500 grams of molten diphenylmethane diisocyanate was placed and, while maintaining a temperature of about 50° C., 0.10 grams of 1,3,5-(N,N-dimethylaminopropyl)-s-hexahydrotriazine was added. The reactor contents were heated at 60° C. for one hour at which time the isocyanate content of the product had decreased to 29.0 percent by weight. Infrared analysis of an aliquot sample indicated the presence of isocyanurate groups. A small amount of benzoyl chloride, equivalent to the amount of trimerization catalyst, was added to deactivate it. Carbodiimidization catalyst (3-methyl-1-phenyl-2-phospholene-1-oxide, 0.015 grams) was then added and the mixture heated at 60° C. for another two hours, at which point the isocyanate content of the mixture was 26.5 percent. The infra-red spectra indicated the presence of carbodiimide, uretonimine isocyanurate and isocyanate groups. At this point, a small amount of trifluoromethanesulfonic acid was added to deactivate the phospholine oxide catalyst. The viscosity of the product was 1200 centipoises at 25° C. and the NCO content was 26.1 percent by weight.

EXAMPLE 8

A reaction vessel equipped as in Example 1 was charged with 500 grams of toluene diisocyanate (2,4'- and 2,6-isomer mixture), 0.032 grams of 3-methyl-1-phenyl-2-phospholene-1-oxide, and 0.06 grams of 1,3,5-tris(N,N-dimethylaminopropyl)-s-hexahydrotriazine. The temperature of the reaction mixture was gradually raised to 80° C. and maintained thereat for one and one-half hours. At this point, the isocyanate content of the mixture was 31.3 percent. Trifluoromethanesulfonic acid, 0.50 gram, was added to deactivate the catalyst. Infra-red analysis of the product indicated the presence of isocyanate, carbodiimide, isocyanurate and uretonimine groups. The Brookfield viscosity of this product was 160 cps at 25° and the NCO content was 31.1 percent by weight.

EXAMPLE 9

Into a one-liter, four-necked reaction vessel equipped with a stirrer, thermometer, air condenser and an inlet for nitrogen gas, was added 500 grams of molten diphenylmethane diisocyanate, pure MDI. Maintaining the pot temperature at 60° C., 0.025 grams of 3-methyl-1-phenyl-2-phospholene-1-oxide and 0.05 grams of 1,3,5-tris(N,N-dimethylaminopropyl)-s-hexahydrotriazine were added simultaneously. The reaction temperature was maintained at 60° C. for one and one-half hours after which a small quantity of trifluoromethane sulfonic acid was added to deactivate the catalyst. The isocyanate content at this point was determined to be 27.2 percent by weight. The Brookfield viscosity of the product was 95 cps. at 25° C. Infra-red analysis of the product indicated presence of isocyanate, isocyanurate, carbodiimide, and uretonimine groups.

Using the polyisocyanates as designated in Table II, microcellular foams were prepared therefrom using the formulations given below.

TABLE II

| Components, parts | Examples | | | | |
|---|---|---|---|---|---|
| | 12 | 13 | 14 | 15 | 16 |
| Polyol A | 100 | 100 | 100 | 100 | 100 |
| 1,4-Butanediol | 25 | 25 | 25 | 25 | 25 |
| L-460 | 2 | 2 | 2 | 2 | 2 |
| T-12 | 0.02 | 0.02 | 0.02 | 0.02 | 0.02 |
| ISONATE 143L | 75.4 | | | | |
| Polyisocyanate of Ex. 2 | — | 80.8 | — | — | — |
| Polyisocyanate of Ex. 1 | — | — | 72.8 | — | — |
| Polyisocyanate of Ex. 4 | — | — | — | 78.4 | — |
| Polyisocyanate of Ex. 3 | — | — | — | — | 73.8 |
| Physical Properties | | | | | |
| Desnity, pcf. | 50.2 | 51.2 | 46.1 | 52.9 | 54.1 |
| Tensile str., psi. | 1300 | 1530 | 1430 | 1590 | 1800 |
| Elongation, % at break | 130 | 80 | 100 | 100 | 120 |
| Split tear, pi. | 109 | 147 | 130 | 132 | 152 |
| Graves tear, pi. | 208 | 320 | 290 | 245 | 295 |
| Shore D Hardness | 40–35 | 47–45 | 45–43 | 48–43 | 46–42 |
| Heat sag, 250° F. | 0.24 | 0.47 | 0.36 | 0.24 | 0.20 |
| Flex recovery | 13/10 | 10/10 | 14/8 | 13/9 | 11/7 |
| Flex modulus, psi. | | | | | |
| −20° F. | 35,500 | 68,100 | 62,700 | 48,900 | 44,900 |
| 72° F. | 12,400 | 20,500 | 20,600 | 17,600 | 15,500 |
| 158° F. | 6,800 | 6,200 | 6,300 | 7,400 | 9,100 |
| ratio −20° F./158° F. | 5.2 | 10.1 | 10.8 | 6.6 | 4.9 |

The physical properties of the microcellular foams prepared employing the polyisocyanates designated above show improved tensile strength, tear strength, hardness and flexural modulus in comparison with the properties of the foam prepared using the prior art polyisocyanate of Example 12.

TABLE III

| Components, parts | Examples | | | | |
|---|---|---|---|---|---|
| | 17 | 18 | 19 | 20 | 21 |
| Polyol B | 100 | 100 | 100 | 100 | 100 |
| 1,4-Butanediol | 25 | 25 | 25 | 25 | 25 |
| L-460 | 2 | 2 | 2 | 2 | 2 |
| T-12 | 0.02 | 0.02 | 0.02 | 0.02 | 0.02 |
| ISONATE 143L | 75.4 | | | | |
| Polyisocyanate of Ex. 2 | — | 80.6 | — | — | — |
| Polyisocyanate of Ex. 1 | — | — | 77.5 | — | — |
| Polyisocyanate of Ex. 4 | — | — | — | 74.6 | — |
| Polyisocyanate of Ex. 3 | — | — | — | — | 73.6 |
| Physical Properties | | | | | |
| Density, pcf. | 50.7 | 55.4 | 49.9 | 55.2 | 56.1 |
| Tensile str., psi. | 1220 | 1460 | 1450 | 1450 | 1740 |
| Elongation, % at break | 60 | 60 | 70 | 50 | 70 |
| Split tear, pi. | 73 | 80 | 101 | 95 | 122 |
| Graves tear, pi. | 151 | 213 | 250 | 200 | 263 |
| Shore D Hardness | 45–42 | 44–42 | 46–44 | 47–40 | 53–50 |
| Heat sag, 250° F. | 0.26 | 0.48 | 0.53 | 0.22 | 0.30 |
| Flex recovery | 16/11 | 11/9 | 12/6 | 13/9 | 15/10 |
| Flex modulus, psi. | | | | | |
| −20° F. | 34,800 | 35,500 | 46,700 | 44,800 | 60,200 |
| 72° F. | 15,000 | 14,000 | 19,200 | 18,200 | 23,500 |
| 158° F. | 8,800 | 6,400 | 8,300 | 10,300 | 14,200 |
| ratio −20° F./158° F. | 3.9 | 5.6 | 5.7 | 4.3 | 4.2 |

The physical properties of the microcellular foams prepared employing the polyisocyanates designated above show improved tensile strength, tear strength, hardness and flexural modulus in comparison with the properties of the foam prepared using the prior art polyisocyanate of Example 17.

The embodiments of the invention in which an exclusive privilege or property is claimed are defined as follows:

1. A highly stable liquid carbodiimide- and uretonimine-isocyanurate-containing polyisocyanate composition prepared by partially trimerizing a mixture of an organic polyisocyanate and a carbodiimide- and uretonimine-containing polyisocyanate in the presence of a catalytic amount of a trimerization catalyst followed by deactivating said trimerization catalyst.

2. A highly stable liquid carbodiimide- and uretonimine-isocyanurate-containing polyisocyanate composition prepared by partially reacting an organic polyisocyanate in the presence of a catalytic amount of a carbodiimization catalyst followed by reacting said carbodiimide- and uretonimine-containing organic polyisocyanate in the presence of a catalytic amount of a trimerization catalyst followed by deactivating said catalysts.

3. A highly stable liquid carbodiimide and uretonimine-isocyanurate-containing polyisocyanate composition prepared by partially reacting an organic polyisocyanate in the presence of a catalytic amount of a trimerization catalyst followed by reacting said isocyanurate-containing organic polyisocyanate in the presence of a catalytic amount of a carbodiimization catalyst followed by deactivating said catalysts.

4. A highly stable liquid carbodiimide- and uretonimine-isocyanurate-containing polyisocyanate composition prepared by partially carbodiimidizing a mixture of an organic polyisocyanate and isocyanurate-containing polyisocyanate in the presence of a catalytic amount of a carbodiimization catalyst followed by deactivating said catalyst.

5. A highly stable liquid carbodiimide- and uretonimine-isocyanurate-containing polyisocyanate composition prepared by heating an organic polyisocyanate in the presence of catalytic amount of a mixture of a carbodiimization catalyst and a trimerization catalyst followed by deactivating said catalysts.

6. A process for the preparation of a stable liquid carbodiimide- and uretonimine-isocyanurate-containing polyisocyanate composition comprising partially trimerizing a mixture of an organic polyisocyanate and carbodiimide- and uretonimine-containing polyisocyanate in the presence of a catalytic amount of a trimerization catalyst followed by deactivating said catalyst.

7. A process for the preparation of a stable liquid carbodiimide- and uretonimine-isocyanurate-containing polyisocyanate composition comprising partially reacting an organic polyisocyanate in the presence of a catalytic amount of a carbodiimidization catalyst followed by reacting said carbodiimide- and uretonimine-containing organic polyisocyanate in the presence of a catalytic amount of a trimerization catalyst followed by deactivating said catalysts.

8. A process for the preparation of a stable liquid carbodiimide- and uretonimine-isocyanurate-containing polyisocyanate composition comprising partially trimerizing an organic polyisocyanate in the presence of a catalytic amount of a trimerization catalyst followed by reacting said isocyanurate-containing organic polyisocyanate in the presence of a catalytic amount of a carbodiimidization catalyst followed by deactivating said catalysts.

9. A process for the preparation of a stable liquid carbodiimide- and uretonimine-isocyanurate-containing polyisocyanate composition comprising partially carbodiimidizing a mixture of polyisocyanurate- and isocyanurate-containing polyisocyanate in the presence of a catalytic amount of a carbodiimidization catalyst followed by deactivating said catalyst.

10. A process for the preparation of a stable liquid carbodiimide- and uretonimine-isocyanurate-containing polyisocyanate composition comprising heating an organic polyisocyanate in the presence of a catalytic amount of a mixture of a carbodiimidization catalyst and a trimerization catalyst followed by deactivating said catalysts.

11. The stable liquid carbodiimide- and uretonimine-isocyanurate-containing polyisocyanate composition of claim 1 wherein the amount of unconverted organic polyisocyanate is from 50 to 99 weight percent of the original total weight of organic polyisocyanate present.

12. The stable liquid carbodiimide- and uretonimine-isocyanurate-containing polyisocyanate composition of claim 2 wherein the amount of unconverted organic polyisocyanate is from 50 to 99 percent of the original total weight of organic polyisocyanate present.

13. The stable liquid carbodiimide- and uretonimine-isocyanurate-containing polyisocyanate composition of claim 3 wherein the amount of unconverted organic polyisocyanate is from 50 to 99 percent of the original total weight of organic polyisocyanate present.

14. The stable liquid carbodiimide- and uretonimine-isocyanurate-containing polyisocyanate composition of claim 4 wherein the amount of unconverted organic polyisocyanate is from 50 to 99 percent of the original total weight of organic polyisocyanate present.

15. The stable liquid carbodiimide- and uretonimine-isocyanurate-containing polyisocyanate composition of claim 5 wherein the amount of unconverted organic polyisocyanate is from 50 to 99 percent of the original total weight of organic polyisocyanate present.

16. The stable liquid carbodiimide- and uretonimine-isocyanurate-containing polyisocyanate composition of claim 1 wherein the amount of polyisocyanurate-containing polyisocyanate is from 1 to 99 weight percent of the modified polyisocyanate content.

17. The stable liquid carbodiimide- and uretonimine-isocyanurate-containing polyisocyanate composition of claim 2 wherein the amount of polyisocyanurate-containing polyisocyanate is from 1 to 99 weight percent of the modified polyisocyanate content.

18. The stable liquid carbodiimide- and uretonimine-isocyanurate-containing polyisocyanate composition of claim 3 wherein the amount of polyisocyanurate-containing polyisocyanate is from 1 to 99 weight percent of the modified polyisocyanate content.

19. The stable liquid carbodiimide and uretonimine-isocyanurate-containing polyisocyanate composition of claim 4 wherein the amount of polyisocyanurate-containing polyisocyanate is from 1 to 99 weight percent of the modified polyisocyanate content.

20. The stable liquid carbodiimide and uretonimine-isocyanurate-containing polyisocyanate composition of claim 5 wherein the amount of polyisocyanurate-containing polyisocyanate is from 1 to 99 weight percent of the modified polyisocyanate content.

21. In the process of claim 6, the trimerization reaction temperature ranges from 25° C. to 230° C.

22. In the process of claim 7, the trimerization reaction temperature ranges from 25° C. to 230° C.

23. In the process of claim 8, the trimerization reaction temperature ranges from 25° C. to 230° C.

24. In the process of claim 9, the trimerization reaction temperature ranges from 25° C. to 230° C.

25. In the process of claim 10, the trimerization reaction temperature ranges from 25° C. to 230° C.

26. In the process of claim 6, the temperature range for the carbodiimide formation ranges from 50° C. to 250° C.

27. In the process of claim 7, the temperature range for the carbodiimide formation ranges from 50° C. to 250° C.

28. In the process of claim 8, the temperature range for the carbodiimide formation ranges from 50° C. to 250° C.

29. In the process of claim 9, the temperature range for the carbodiimide formation ranges from 50° C. to 250° C.

30. In the process of claim 10, the temperature range for the carbodiimide formation ranges from 50° C. to 250° C.

31. In a process for the manufacture of microcellular foams by the reaction of organic polyisocyanates and polyols, catalysts, cross-linking agents, surfactants, and additives, wherein the improvement comprises a highly stable organic polyisocyanate prepared by partially trimerizing a mixture of an organic polyisocyanate and carbodiimide- and uretonimine-containing polyisocyanate in the presence of a catalytic amount of a trimerization catalyst followed by deactivating said catalyst.

32. In a process for the manufacture of microcellular foams by the reaction of organic polyisocyanates and polyols, catalysts, cross-linking agents, surfactants, and additives, wherein the improvement comprises a highly stable organic polyisocyanate prepared by partially reacting said organic polyisocyanate in the presence of a catalytic amount of a carbodiimidization catalyst followed by reacting said and carbodiimide- and uretonimine-containing organic polyisocyanate in the presence of a catalytic amount of a trimerization catalyst followed by deactivating said catalysts.

33. In a process for the manufacture of microcellular foams, by the reaction of organic polyisocyanates and polyols, catalysts, cross-linking agents, surfactants, and additives, wherein the improvement comprises a highly stable organic polyisocyanate prepared by partially trimerizing an organic polyisocyanate in the presence of a trimerization catalyst followed by reacting said isocyanurate-containing organic polyisocyanate in the presence of a catalytic amount of a carbodiimization catalyst followed by deactivating said catalysts.

34. In a process for the manufacture of microcellular foams, by the reaction of organic polyisocyanates and polyols, catalysts, cross-linking agents, surfactants, and additives, wherein the improvement comprises a highly stable organic polyisocyanate prepared by partially carbodiimidizing a mixture of polyisocyanate- and isocyanurate-containing polyisocyanate in the presence of a catalytic amount of a carbodiimization catalyst followed by deactivating said catalyst.

35. In a process for the manufacture of microcellular foams, by the reaction of organic polyisocyanates and polyols, catalysts, cross-linking agents, surfactants, and additives, wherein the improvement comprises a highly stable organic polyisocyanate prepared by heating said polyisocyanate in the presence of a catalytic amount of a mixture of a carbodiimization catalyst and a trimerization catalyst followed by deactivating said catalysts.

36. In the process of claim 31, the trimerization reaction temperature ranges from 25° C. to 230° C.

37. In the process of claim 32, the trimerization reaction temperature ranges from 25° C. to 230° C.

38. In the process of claim 33, the trimerization reaction temperature ranges from 25° C. to 230° C.

39. In the process of claim 34, the trimerization reaction temperature ranges from 25° C. to 230° C.

40. In the process of claim 35, the trimerization reaction temperature ranges from 25° C. to 230° C.

41. In the process of claim 31, the temperature range for the carbodiimide formation ranges from 50° C. to 250° C.

42. In the process of claim 32, the temperature range for the carbodiimide formation ranges from 50° C. to 250° C.

43. In the process of claim 33, the temperature range for the carbodiimide formation ranges from 50° C. to 250° C.

44. In the process of claim 34, the temperature range for the carbodiimide formation ranges from 50° C. to 250° C.

45. In the process of claim 35, the temperature range for the carbodiimide formation ranges from 50° C. to 250° C.

46. In the process of claim 31, the amount of unconverted organic polyisocyanate is from 50 to 99 weight percent of the original total weight of organic polyisocyanate present.

47. In the process of claim 32, the amount of unconverted organic polyisocyanate is from 50 to 99 percent of the original total weight of organic polyisocyanate present.

48. In the process of claim 33, the amount of unconverted organic polyisocyanate is from 50 to 99 percent of the original total weight of organic polyisocyanate present.

49. In the process of claim 34, the amount of unconverted organic polyisocyanate is from 50 to 99 percent of the original total weight of organic polyisocyanate present.

50. In the process of claim 35, the amount of unconverted organic polyisocyanate is from 50 to 99 percent of the original total weight of organic polyisocyanate present.

* * * * *